(12) United States Patent
Kawakami et al.

(10) Patent No.: US 10,849,862 B2
(45) Date of Patent: Dec. 1, 2020

(54) FORMULATION OF CURCUMIN AND ANTI-PD-1 ANTIBODY

(71) Applicant: THERAVALUES CORPORATION, Tokyo (JP)

(72) Inventors: Yutaka Kawakami, Shinjuku-ku (JP); Tomonori Yaguchi, Shinjuku-ku (JP); Taeko Hayakawa, Shinjuku-ku (JP); Atsushi Imaizumi, Hino (JP)

(73) Assignee: THERAVALUES CORPORATION, Tokyo (JP)

( * ) Notice: Subject to any disclaimer, the term of this patent is extended or adjusted under 35 U.S.C. 154(b) by 8 days.

(21) Appl. No.: 15/539,920

(22) PCT Filed: Dec. 24, 2015

(86) PCT No.: PCT/JP2015/086133
§ 371 (c)(1),
(2) Date: Jun. 26, 2017

(87) PCT Pub. No.: WO2016/104657
PCT Pub. Date: Jun. 30, 2016

(65) Prior Publication Data
US 2017/0367997 A1 Dec. 28, 2017

(30) Foreign Application Priority Data
Dec. 26, 2014 (JP) .................. 2014-264359

(51) Int. Cl.
| | | |
|---|---|---|
| *A61K 31/12* | (2006.01) | |
| *A61K 39/395* | (2006.01) | |
| *A61K 45/06* | (2006.01) | |
| *C07K 16/28* | (2006.01) | |
| *C07K 16/30* | (2006.01) | |
| *A61K 39/00* | (2006.01) | |

(52) U.S. Cl.
CPC .......... *A61K 31/12* (2013.01); *A61K 39/3955* (2013.01); *A61K 45/06* (2013.01); *C07K 16/2818* (2013.01); *C07K 16/2827* (2013.01); *C07K 16/30* (2013.01); *A61K 2039/505* (2013.01); *C07K 2317/24* (2013.01); *C07K 2317/76* (2013.01)

(58) Field of Classification Search
CPC ........................... A61K 31/12; A61K 39/3955
USPC ........................................................ 424/133.1
See application file for complete search history.

(56) References Cited

U.S. PATENT DOCUMENTS

2005/0049299 A1* 3/2005 Aggarwal .............. A61K 31/12
514/456
2006/0110383 A1 5/2006 Honjo et al.
2009/0297518 A1 12/2009 Honjo et al.
2016/0326593 A1* 11/2016 Clement .............. C12Q 1/6869
2018/0271891 A1* 9/2018 Garraway .............. A61K 45/06

FOREIGN PATENT DOCUMENTS

| JP | 11-92363 A | 4/1999 |
| JP | 4409430 B2 | 2/2010 |
| JP | 2014-65748 A | 4/2014 |

OTHER PUBLICATIONS

Xu et al., (J Exp Clin Cancer Res. Oct. 29, 2018;37(1):261.*
NCI Drug Dictionary definition "Nivolumab" (pp. 1-2; Feb. 13, 2019).*
Liao et al (Arch Oral Biol. Aug. 2018;92:32-37; Epub Apr. 30, 2018; Abstract only).*
Lim et al.(Cancer Cell. Dec. 12, 2016; 30(6): 925-939).*
Shao et al. (OncoTargets and Therapy 2017:10 2675-2683).*
Modasiya et al. (Int. J. of Pharm. & Life Sci. (IJPLS), vol. 3, Issue 3: Mar. 2012, 1490-1497).*
Priyadarsini (Molecules Dec. 1, 2014, 19: 20091-20112).*
Thereavalues product data sheet for "Theracumin" (pp. 1-10; Apr. 29, 2020).*
Kanai (World J Gastroenterol Jul. 28, 2014; 20(28): 9384-9391).*
Jennifer Couzin-Frankel. "Cancer Immunotherapy," Science, vol. 342, Dec. 20, 2013. (3 pages).
Suzanne L. Topalian, et al., Safety, Activity, and Immune Correlates of Anti-PD-1 Antibody in Cancer, The new England Journal of Medicine, vol. 366. No. 26, Jun. 28. 2012, pp. 2443-2454.
Taeko Hayakawa, et al., "Enhanced anti-tumor effects of the PD-1/PD-L1 blockade by combining a highly absorptive form of NF-kB/STAT3 inhibitor curcumin." Journal for ImmunoTherapy of Cancer, vol. 2. Suppl 3, Nov. 6, 2014, p. 210.
Taeko Hayakawa, et al., "Deeper insights into cancer biology bringing cures for cancer patients." The 73rd Annual Meeting of the Japanese Cancer Association, Sep. 2014, (4 pages) (with English abstract).
Taeko Hayakawa, et al., "Enhanced effects of immune-checkpoint blockade therapy via improvement effect of immunosuppression by using highly absorptive curcumin in combination," The 18th Annual Meeting of Japanese Association of Cancer Immunology, 2014, (8 pages) (with partial English translation).
International Search Report dated Mar. 1, 2016 in PCT/JP2015/086133 filed Dec. 24, 2015.
Office Acton as received in the corresponding Japanese Patent Application No. 2016-566478 dated Sep. 17, 2019 w/English Translation.

* cited by examiner

*Primary Examiner* — Lynn A Bristol
(74) *Attorney, Agent, or Firm* — Oblon, McClelland, Maier & Neustadt, L.L.P.

(57) ABSTRACT

To provide a therapeutic agent for cancer having a higher therapeutic effect. A therapeutic agent for cancer, containing: at least one selected from the group consisting of curcumin and a derivative thereof; and at least one selected from the group consisting of an anti-PD-1 antibody, an anti-PD-L1 antibody, and an anti-PD-L2 antibody in combination.

8 Claims, 6 Drawing Sheets

[Fig. 1]
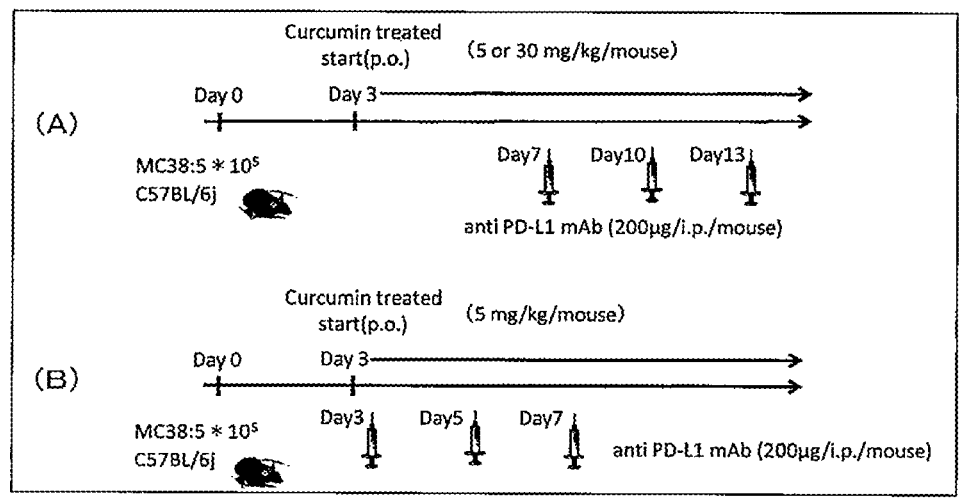
[Fig. 2]
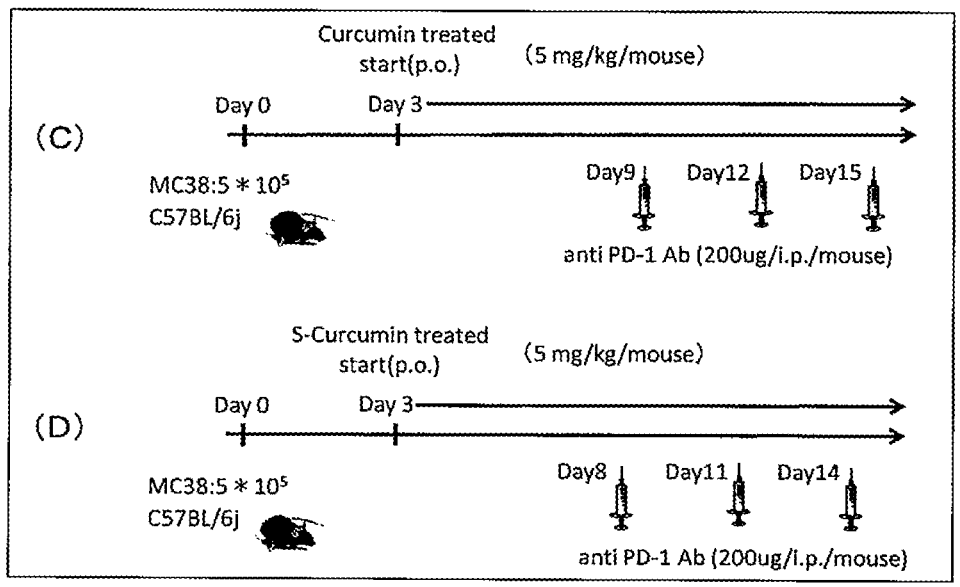

[Fig. 3]
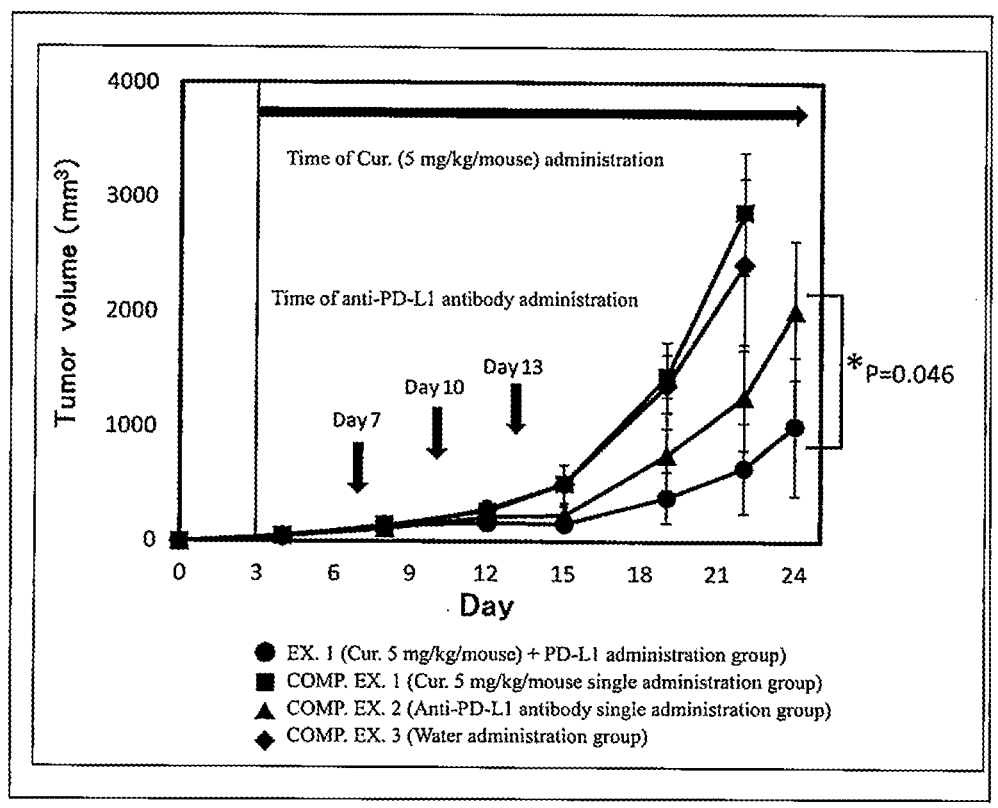

[Fig. 4]
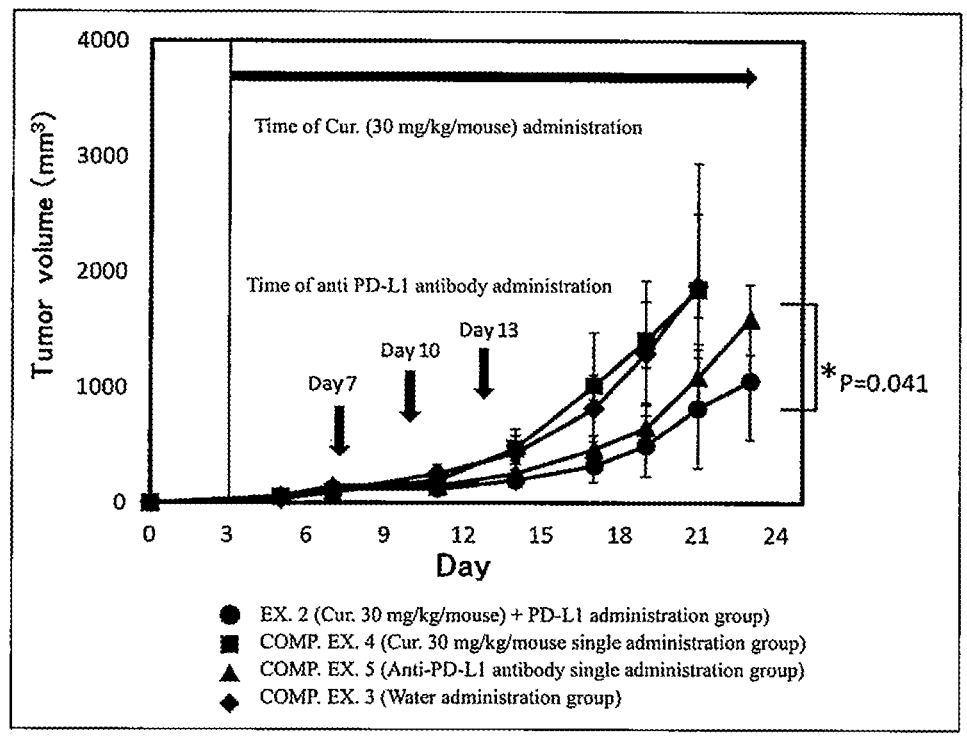

[Fig. 5]
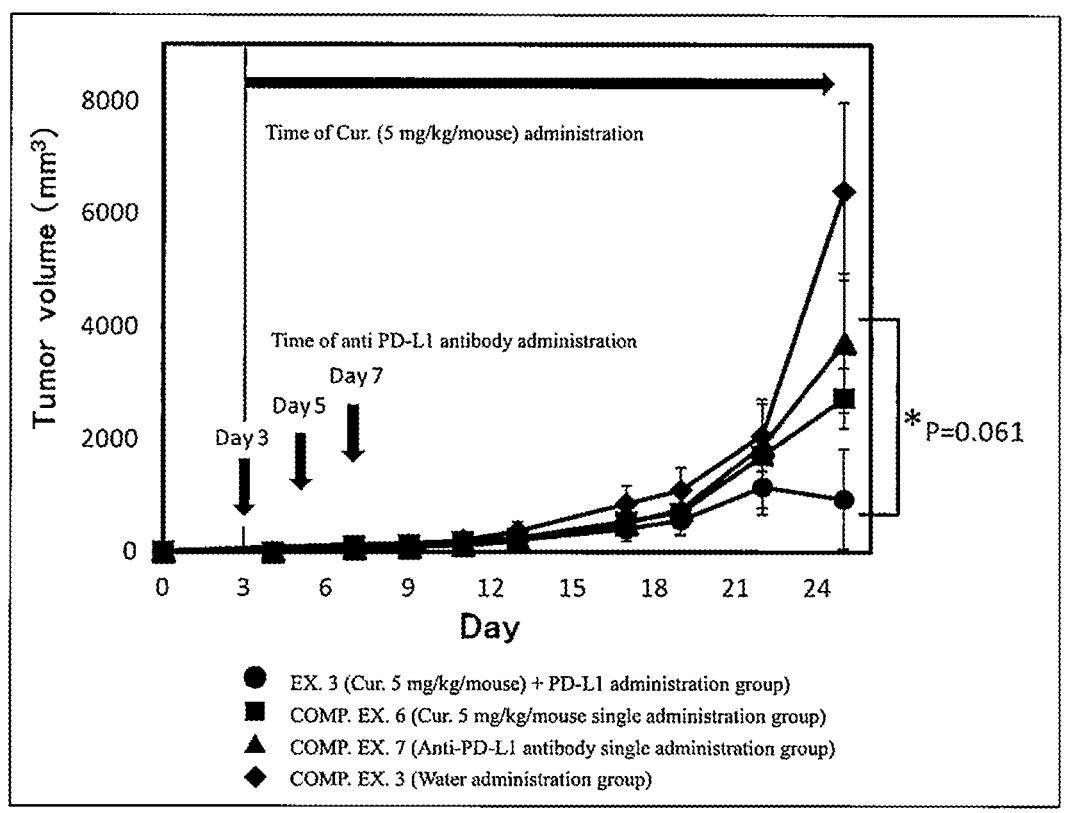

[Fig. 6]
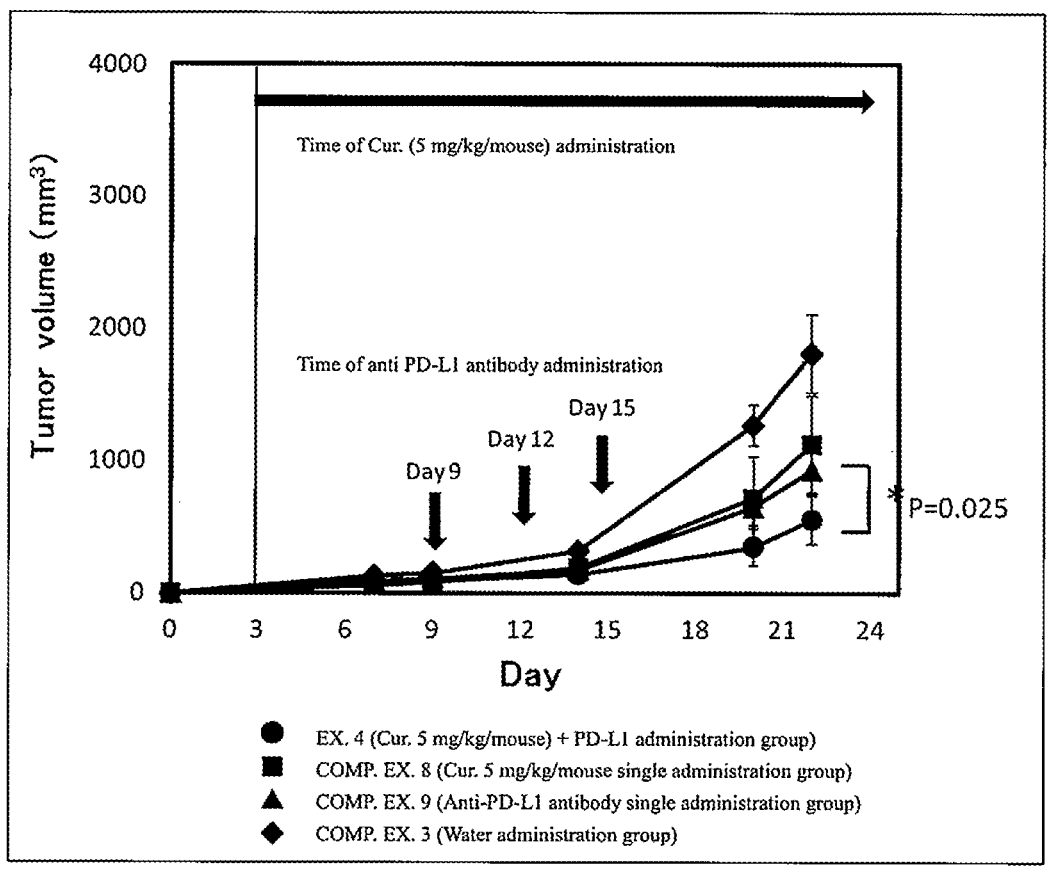

[Fig. 7]
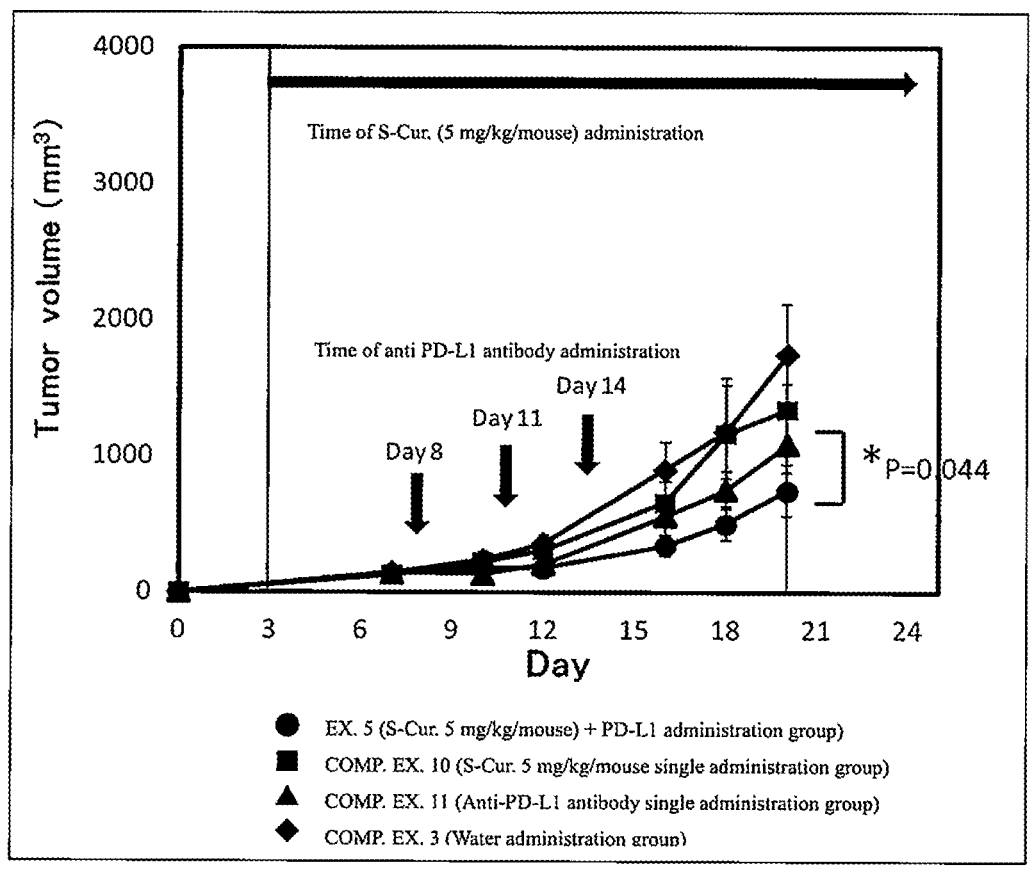

FORMULATION OF CURCUMIN AND ANTI-PD-1 ANTIBODY

TECHNICAL FIELD

The present invention relates to a novel therapeutic agent for cancer.

BACKGROUND ART

Currently, in addition to surgery, chemotherapy, and radiation therapy, which are standard treatments for cancer, cancer immunotherapy has been developed as one of the novel cancer treatments, and the therapeutic effects are recognized (Non Patent Literature 1).

In general, activation of T cells is controlled positively or negatively by the stimulation through an antigen receptor (TCR) expressed on the cell membrane, and by the co-stimulation through a co-stimulatory molecule group. The activated T cells are suppressed by a molecule such as CTLA-4, and PD-1, which act as negative feedback, and by using this mechanism, cancer cells suppress the activated T cells, and result in escaping from the immune surveillance mechanism, and continuing to proliferate.

Therefore, as to a method for avoiding the suppression of T cells by cancer cells, it is considered to be effective for the cancer treatment that the T-cell activation is induced by the treatment with inhibitory antibodies against the inhibitory co-stimulatory molecule on T cells, and in Patent Literatures 1 and 2, as a new target in the cancer treatment, focusing on PD-1 (expressed on T cells), and PD-L1 or PD-L2 (expressed on cancer cells), which are involved in suppression of T cells, a technique relating to recovery of immune function by a substance that inhibits PD-1, PD-L1, or PD-L2, and further a technique relating to a therapeutic agent for cancer containing an anti-PD-1 antibody, an anti-PD-L1 antibody, or an anti-PD-L2 antibody based on the proliferation suppression of cancer cells through the activation mechanism have been disclosed.

CITATION LIST

Patent Literature

Patent Literature 1: JP 4409430 B1
Patent Literature 2: JP 2014-65748 A

Non Patent Literature

Non Patent Literature 1: Couzin-Frankle J. et al., Science, 2013, 20; 342(6165): 1432-1433
Non Patent Literature 2: Topalian S L et al., N. Engl. J. Med., 2012, 28; 366(26): 2443-2454

SUMMARY OF THE INVENTION

Technical Problem

Although a high therapeutic effect has been recognized in the above-described antibody medicines in recent years, there are some cases where no effect can be obtained, and also some cases where sufficient effects are not recognized (Non Patent Literature 2), and development of a novel method to make an effect in these cases is a problem.

Solution to Problem

Accordingly, as a result of various studies on measures for further improving the anti-tumor effects of the antibody medicines, the present inventors have found wholly unexpectedly that when the antibody medicines, and curcumin or a derivative thereof are used in combination, the anti-tumor effect is synergistically enhanced and the proliferation of cancer cells is remarkably suppressed, and thus have completed the present invention.

That is, the present invention is to provide the following inventions [1] to [9].

[1] A therapeutic agent for cancer, comprising: one or more selected from the group consisting of curcumin and a derivative thereof; and one or more selected from the group consisting of an anti-PD-1 antibody, an anti-PD-L1 antibody, and an anti-PD-L2 antibody in combination.

[2] The therapeutic agent for cancer according to [1], wherein the derivative of curcumin is one or more selected from the group consisting of bisdesmethoxycurcumin, desmethoxycurcumin, and tetrahydrocurcumin.

[3] The therapeutic agent for cancer according to [1] or [2], wherein 10 mg to 10 g of one or more selected from the group consisting of curcumin and a derivative thereof is combined as a daily dose.

[4] The therapeutic agent for cancer according to any one of [1] to [3], wherein each of the anti-PD-1 antibody, the anti-PD-L1 antibody, and the anti-PD-L2 antibody is a humanized antibody.

[5] The therapeutic agent for cancer according to any one of [1] to [4], further comprising: an immunostimulant; and/or a cancer chemotherapeutic agent in combination.

[6] The therapeutic agent for cancer according to any one of [1] to [5], comprising: a pharmaceutical preparation containing one or more selected from the group consisting of curcumin and a derivative thereof; and a pharmaceutical preparation containing one or more selected from the group consisting of an anti-PD-1 antibody, an anti-PD-L1 antibody, and an anti-PD-L2 antibody in combination.

[7] A combination comprising: one or more selected from the group consisting of curcumin and a derivative thereof; and one or more selected from an anti-PD-1 antibody, an anti-PD-L1 antibody, and an anti-PD-L2 antibody, for treating cancer.

[8] Use of a combination of: one or more selected from the group consisting of curcumin and a derivative thereof; and one or more selected from the group consisting of an anti-PD-1 antibody, an anti-PD-L1 antibody, and an anti-PD-L2 antibody, for preparing a therapeutic agent for cancer.

[9] A method for treating cancer, comprising administering simultaneously or separately one or more selected from the group consisting of curcumin and a derivative thereof and one or more selected from the group consisting of an anti-PD-1 antibody, an anti-PD-L1 antibody, and an anti-PD-L2 antibody.

Effects of Invention

By using the therapeutic agent for cancer of the present invention, a cancer cell antiproliferative effect that is particularly remarkably excellent as compared with a case of single administration of an anti-PD-1 antibody, an anti-PD-L1 antibody, or an anti-PD-L2 antibody is obtained.

BRIEF DESCRIPTION OF DRAWINGS

FIG. 1 is a drawing showing schedule of the administration of Examples 1 to 3.

FIG. 2 is a drawing showing schedule of the administration of Examples 4 to 5.

FIG. 3 is a drawing showing influence on the proliferation of MC38 mouse colon cancer cells due to the combination of curcumin (5 mg/kg/mouse) and an anti-PD-L1 antibody.

FIG. 4 is a drawing showing influence on the proliferation of MC38 mouse colon cancer cells due to the combination of curcumin (30 mg/kg/mouse) and an anti-PD-L1 antibody.

FIG. 5 is a drawing showing influence on the proliferation of MC38 mouse colon cancer cells due to the time of administration of an anti-PD-L1 antibody under different curcumin administration conditions.

FIG. 6 is a drawing showing influence on the proliferation of MC38 mouse colon cancer cells due to the combination of curcumin (5 mg/kg/mouse) and an anti-PD-1 antibody.

FIG. 7 is a drawing showing influence on the proliferation of MC38 mouse colon cancer cells due to the combination of synthetic curcumin (5 mg/kg/mouse) and an anti PD-1 antibody.

DESCRIPTION OF EMBODIMENTS

The active components of the therapeutic agent for cancer of the present invention are both of (A) one or more selected from the group consisting of curcumin and a derivative thereof, and (B) one or more selected from the group consisting of an anti-PD-1 antibody, an anti-PD-L1 antibody, and an anti-PD-L2 antibody.

(A) Curcumin is a main component of curcuminoid contained in turmeric pigment, and is a compound represented by the following structural formula (1).

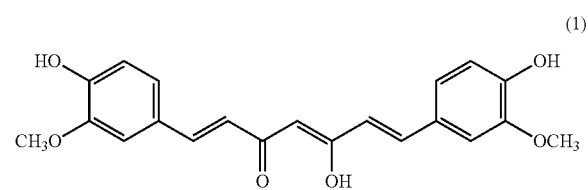

As the curcumin used in the present invention, chemically synthesized curcumin may be used; or those distributed as turmeric pigment may also be used. Examples of the turmeric pigment include powdered turmeric obtained by pulverizing the dried rhizome of *Curcuma longa* LINNE, crude curcumin obtained by extracting the powdered turmeric with an appropriate solvent (for example, ethanol, fat and oil, propylene glycol, hexane, and acetone) or oleoresin (turmeric oleoresin), and purified curcumin.

In addition, curcumin includes both of a keto form of curcumin and an enol form of curcumin, which are tautomers.

Examples of the curcumin derivative include desmethoxycurcumin, bisdesmethoxycurcumin, tetrahydrocurcumin, and dihydroxytetrahydrocurcumin. In addition, in turmeric pigment, curcumin, desmethoxycurcumin, and bisdesmethoxycurcumin are contained. As the curcumin derivative, one or more selected from the group consisting of desmethoxycurcumin, bisdesmethoxycurcumin and tetrahydrocurcumin are preferable.

As (A) one or more selected from the group consisting of curcumin and a derivative thereof, a turmeric extract is preferably used, and a turmeric pigment containing one or more selected from the group consisting of curcumin and a derivative thereof is more preferably used. As a commercially available product of the turmeric pigment containing one or more selected from the group consisting of curcumin and a derivative thereof, there is no particular limitation as long as one or more selected from the group consisting of curcumin and a derivative thereof are contained, but the one having high absorbability into the body is preferred, and THERACURMIN® (manufactured by Theravalues Corporation) is particularly preferred. Further, as the one or more selected from the group consisting of curcumin and a derivative thereof, crystals may be used, or amorphous ones may also be used, but from the viewpoint of the high absorbability into the body, amorphous curcumin is preferred, and in particular, an amorphous curcumin complex of curcumin, and one or more selected from the group consisting of hydroxypropyl methyl cellulose and hydroxypropyl cellulose is preferred.

(B) One or more selected from the group consisting of an anti-PD-1 antibody, an anti-PD-L1 antibody, and an anti-PD-L2 antibody are, for example, the antibodies described in Patent Literatures 1 and 2.

As these antibodies, an antibody against PD-1, PD-L1, or PD-L2, which inhibits immunosuppressive signals by PD-1, PD-L1, or PD-L2, is preferred, and in particular, one having an action of suppressing the proliferation of cancer cells is preferred. In addition, these antibodies may be any antibody of a human-derived antibody, a mouse-derived antibody, a rat-derived antibody, a rabbit-derived antibody, or a goat-derived antibody, and further may also be any antibody of a polyclonal or monoclonal antibody, a complete or truncated (for example, a F(ab')$_2$, Fab', Fab, or Fv fragment) antibody, a chimeric antibody, a humanized antibody, or a completely human antibody, of the human-derived antibody, the mouse-derived antibody, the rat-derived antibody, the rabbit-derived antibody, or the goat-derived antibody. More preferably, a humanized antibody or a completely human antibody, and a monoclonal antibody are used.

These antibodies can be produced by the methods described in Patent Literatures 1 and 2. An anti-PD-1 antibody has already been commercially available as a medicament, and the commercially available one can also be used. Further, preferably an anti-PD-1 antibody or an anti-PD-L1 antibody is used, and more preferably an anti-PD-L1 antibody is used.

The therapeutic agent for cancer of the present invention may be one formulated into one dosage form by mixing the component (A) and the component (B), or may also be a separate pharmaceutical preparation containing each of the components so that the component (A) and the component (B) can be administered simultaneously or separately. In addition, in a case of a separate pharmaceutical preparation, both may be made as a kit preparation to be supplied together. In the present invention, it is preferred to use a separate pharmaceutical preparation so that the component (A) and the component (B) can be administered simultaneously or separately.

The dosage form of the pharmaceutical preparation is not particularly limited, and for example, a preparation for oral administration, an injection, a suppository, a patch preparation, and ointment can be mentioned. In order to prepare a separate pharmaceutical preparation in which the component (A) and the component (B) are separately contained, the dosage form of each of the component (A) and the component (B) may be different from each other, or may be the same as each other. For example, the following can be accepted: each of the component (A) and the component (B) is contained separately in a preparation for oral administration; the component (A) is contained in a preparation for oral administration, and the component (B) is contained in an injection; the component (A) is contained in an injection, and the component (B) is contained in a preparation for oral administration; or each of the component (A) and the component (B) is contained separately in an injection, but it is preferred that the component (A) is contained in a preparation for oral administration, and the component (B) is contained in an injection.

Examples of the preparation for oral administration include a tablet, a coated tablet, powders, granules, a capsule, and a liquid. For preparing a preparation for oral administration, a pharmaceutically acceptable carrier, for example, an excipient, a binder, a disintegrant, a lubricant, a diluent, a stabilizer, a coloring agent, a flavoring agent, and a scenting agent may be mixed.

Examples of the injection include an intravenous injection, a subcutaneous injection, and an intramuscular injection, but an intravenous injection is more preferred. In the preparation of an injection, a pharmaceutically acceptable carrier, for example, a buffer agent, a diluent, a solubilizer, a suspending agent, a pH adjusting agent, a stabilizer, an isotonizing agent, and an analgesic may be mixed.

Examples of the excipient include lactose, sucrose, sodium chloride, glucose, maltose, mannitol, erythritol, xylitol, maltitol, inositol, dextran, sorbitol, albumin, urea, starch, calcium carbonate, kaolin, crystal cellulose, silicic acid, methyl cellulose, glycerin, sodium alginate, and gum arabic, and a mixture thereof. Examples of the lubricant include purified talc, stearate, borax, and polyethylene glycol, and a mixture thereof. Examples of the binder include simple syrup, a glucose solution, a starch solution, a gelatin solution, polyvinyl alcohol, polyvinyl ether, polyvinyl pyrrolidone, carboxymethyl cellulose, shellac, methyl cellulose, ethyl cellulose, water, ethanol, and potassium phosphate, and a mixture thereof.

Examples of the disintegrant include dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose, and a mixture thereof. Examples of the diluent include water, ethyl alcohol, macrogol, propylene glycol, ethoxylated isostearyl alcohol, polyoxylated isostearyl alcohol, and polyoxyethylene sorbitan fatty acid esters, and a mixture thereof. Examples of the stabilizer include sodium pyrosulfite, ethylenediaminetetraacetic acid, thioglycolic acid, and thiolactic acid, and a mixture thereof. Examples of the isotonizing agent include sodium chloride, boric acid, glucose, and glycerin, and a mixture thereof. Examples of the pH adjusting agent and buffer agent include sodium citrate, citric acid, sodium acetate, and sodium phosphate, and a mixture thereof. Examples of the analgesic agent include procaine hydrochloride, and lidocaine hydrochloride, and a mixture thereof.

The dose of the component (A) in the cancer therapeutic agent of the present invention is, as an adult daily dose of curcumin and a derivative thereof, preferably 10 mg to 10 g, and more preferably 30 mg to 10 g. On the other hand, the dose of the component (B) in the cancer therapeutic agent of the present invention is, as an adult daily dose of the component (B), preferably 1 µg to 100 mg. In addition, as the therapeutic agent for cancer of the present invention, the components (A) and (B) may be divided to be administered once to several times per day.

The cancer to which the therapeutic agent for cancer of the present invention is applied is not particularly limited, but cancer expressing PD-L1 and/or PD-L2 is preferred. Specific examples of the cancer include colon/rectal cancer, liver cancer, kidney cancer, head and neck cancer, esophageal cancer, gastric cancer, biliary tract cancer, gallbladder/bile duct cancer, pancreatic cancer, lung cancer, breast cancer, ovarian cancer, cervical cancer, endometrial cancer, bladder cancer, prostate cancer, testicular tumor, bone/soft tissue sarcoma, leukemia, malignant lymphoma, multiple myeloma, skin cancer, brain tumor, and testicular tumor.

In the therapeutic agent for cancer of the present invention, an adjuvant, and/or a cancer chemotherapeutic agent may be combined.

Examples of the adjuvant include various kinds of cytokines, and tumor antigens. Examples of the cytokine stimulating immune response include GM-CSF, M-CSF, G-CSF, interferon-α, interferon-β, interferon-γ, IL-1, IL-2, IL-3, and IL-12. Further, a B7 ligand derivative, an anti-CD3 antibody, an anti-CD28 antibody, and an anti-CTLA-4 antibody can also increase the immune response.

Examples of the cancer chemotherapeutic agent include an alkylating agent, a nitrosourea agent, an antimetabolite, an anticancer antibiotic, a plant-derived alkaloid, a topoisomerase inhibitor, a hormone therapy agent, a hormone antagonist, an aromatase inhibitor, a P-glycoprotein inhibitor, a platinum complex derivative, and other immunotherapeutic agents, or other anticancer agents.

EXAMPLES

Hereinafter, the present invention will be described in more detail by way of Examples.

Examples 1 to 5, and Comparative Examples 1 to 11

A. Method
(1) Test Animals

As the test animals, 6-week old C56BL/6j mice (female, weighed around 20 g, CLEA Japan, Inc.) were purchased, and used after being acclimated to the environment for two to five days.

(2) Transplantation Method

In the right abdomen of the test animals, $5 \times 10^5$ mouse colon cancer cell lines (MC38) were subcutaneously implanted by using a 27 G needle.

(3) Administration Method

Into the mice (n=5 to 8) to which the colon cancer cell lines (MC 38) had been inoculated, every day from the 3rd day after the inoculation to the last day of the experiment, 200 µl of a curcumin solution prepared by suspending a commercially available curcumin 10%-containing pharmaceutical preparation (THDRACURMIN® CR-031P, manufactured by Theravalues Corporation) (Examples 1 to 4) in water or by suspending the synthetic curcumin-HPMC complex prepared as described below (Example 5) in water (prepared so that the curcumin content is 5 mg or 30 mg per 1 kg body weight) was forcibly administered orally to the mice using a feeding needle. Further, as shown in FIG. 1, an anti-PD-L1 antibody (200 µl/100 µl/mouse) was intraperitoneally administered on the 3rd, 5th, and 7th days after the inoculation ((A) in FIG. 1), or on the 7th, 10th, and 13th days after the inoculation ((B) in FIG. 1), or as shown in FIG. 2, an anti-PD-1 antibody (200 µg/100 µl/mouse) was intraperitoneally administered on the 8th, 11th, and 14th days after the inoculation ((C) in FIG. 2), or on the 9th, 12th, and 15th days after the inoculation ((D) in FIG. 2), the tumor size of the mice was examined with the lapse of time (Examples 1 to 5).

In addition, as to the control groups, a curcumin single administration group (Comparative Examples 1, 4, 6, 8 and 10) in a case where Rat IgG2b (clone: LTF-2 manufactured by Bio X Cell) was intraperitoneally administered in place of the anti-PD-L1 antibody (clone: 10F.9G2 manufactured by Bio X Cell) or the anti-PD-1 antibody (clone: RMP1-14 manufactured by Bio X Cell); an anti-PD-L1 antibody single administration group (Comparative Examples 2, 5 and 7) in a case where water was administered in place of the curcumin solution, and an anti-PD-L1 antibody was administered; an anti-PD-1 antibody single administration group (Comparative Examples 9 and 11) in a case where water was administered in place of the curcumin solution, and an anti-PD-1 antibody was administered; and a water administration group (Comparative Example 3) in a case where water was administered in place of the curcumin solution, and Rat IgG2b (clone: LTF-2 manufactured by Bio X Cell) was administered in place of the anti-PD-L1 antibody were prepared.

(4) Evaluation of Tumor Size

The tumor size of the test animals was measured by measuring the long diameter and the short diameter of the tumor with a vernier caliper every 2 to 4 days, and calculated by the following equation.

$$\text{Tumor size} = \text{the long diameter} \times \text{the short diameter} \times \text{the short diameter} \div 2 \quad \text{(Mathematical Formula 1)}$$

(5) Preparation Method of Synthetic Curcumin-HPMC Complex

Into 167 mL of pure water, 12 g of hydroxypropyl methyl cellulose (HPMC: METOLOSE® SE-06, manufactured by Shin-Etsu Chemical Co., Ltd.) was dissolved to prepare a HPMC solution. On the other hand, 6.0 g of synthetic curcumin (C2302, manufactured by TOKYO CHEMICAL INDUSTRY CO., LTD.) was dissolved into 50 mL of a 1 mol/L aqueous sodium hydroxide solution (pH 14) to prepare a curcumin solution. After that, the HPMC solution and the synthetic curcumin solution were mixed, and the pH of the mixture solution was adjusted to 6 using a 10 mol/L aqueous hydrochloric acid solution to prepare a solution containing a complex of synthetic curcumin containing amorphous curcumin and hydroxypropyl methyl cellulose.

Next, the solution containing the complex was spray-dried by using a spray dryer ADL311S (manufactured by Yamato Scientific Co., Ltd.) under the conditions of an inlet temperature of 60° C., an outlet temperature of 75° C., a spray pressure of 0.12 MPa, and a feed rate of 6 to 7 mL/min to prepare synthetic curcumin containing powdered amorphous curcumin and hydroxypropyl methyl cellulose.)

B. Results (1) The influence on the proliferation of MC38 mouse colon cancer tumor due to the combination of curcumin (5 mg/kg/mouse) and an anti-PD-L1 antibody was examined.

As shown in FIG. 3, the size of the MC38 mouse colon cancer tumor was 1010 mm$^3$ (the 24th day after the inoculation) in a case where curcumin (5 mg/kg/mouse) and an anti-PD-L1 antibody were used in combination (Example 1), and showed a significantly smaller value as compared with 2019 mm$^3$ (the 24th day after the inoculation) in a case where the anti-PD-L1 antibody was singly alone administered, and a remarkable antiproliferative effect of the colon cancer tumor was recognized.

On the other hand, in a case where curcumin (5 mg/kg/mouse) was singly alone administered, the size of the MC38 mouse colon cancer tumor showed the same size as that of the control, and an antiproliferative effect of the colon cancer tumor was not recognized by curcumin single administration.

(2) The influence on the proliferation of MC38 mouse colon cancer tumor due to the combined use of curcumin (30 mg/kg/mouse) and an anti-PD-L1 antibody was examined.

As shown in FIG. 4, the size of the MC38 mouse colon cancer tumor was 1062 mm$^3$ (the 23rd day after the inoculation) in a case where curcumin (30 mg/kg/mouse) and an anti-PD-L1 antibody were used in combination (Example 2), and showed a significantly smaller value as compared with 1595 mm$^3$ (the 24th day after the inoculation) in a case where the anti-PD-L1 antibody was singly administered, and a remarkable antiproliferative effect of the colon cancer tumor was recognized.

On the other hand, in a case where curcumin (30 mg/kg/mouse) was singly alone administered, the size of the MC38 mouse colon cancer tumor showed the same size as that of the control, and an antiproliferative effect of the colon cancer tumor was not recognized by curcumin single administration.

From the above, it was found that by using curcumin in combination when an anti-PD-L1 antibody is administered, a remarkable antiproliferative effect of the MC38 mouse colon cancer tumor is obtained by a synergistic effect of both.

(3) For the purpose of examining the influence on the proliferation of MC38 mouse colon cancer tumor due to the time of administration of an anti-PD-L1 antibody under the curcumin administration conditions, the time of administration of the anti-PD-L1 antibody was set to the 3rd, 5th, and 7th days after the inoculation, the proliferation aspect of the MC38 mouse colon cancer tumor due to the combination of curcumin and an anti-PD-L1 antibody was examined in the similar manner as in Test Example 1 (the timing of administration of the anti-PD-L1 antibody in Test Example 1 is the 7th, 10th, and 13th days after the inoculation).

As a result, as shown in FIG. 5, the size of the MC38 mouse colon cancer tumor was 945 mm$^3$ (the 25th day after the inoculation) in a case where curcumin (5 mg/kg/mouse) and an anti-PD-L1 antibody were used in combination (Example 3), and showed a significantly smaller value as compared with 3716 mm$^3$ (the 25th day after the inoculation) in a case where the anti-PD-L1 antibody was singly administered, and even when the administration of the anti-PD-L1 antibody was started at the same time as the curcumin administration, a remarkable antiproliferative effect of the colon cancer tumor was recognized.

From the above, it was found that regardless of the time of the administration of the anti-PD-L1 antibody, a remarkable antiproliferative effect of the MC38 mouse colon cancer tumor is obtained by a synergistic effect of the curcumin and the anti-PD-L1 antibody.

(4) The influence on the proliferation of MC38 mouse colon cancer tumor due to the combined use of curcumin (5 mg/kg/mouse) and an anti-PD-1 antibody was examined.

As shown in FIG. 6, the size of the MC38 mouse colon cancer tumor showed a significantly smaller value in a case where curcumin (5 mg/kg/mouse) and an anti-PD-1 antibody were used in combination (Example 4) as compared with that in a case where the anti-PD-1 antibody was singly administered, and a remarkable antiproliferative effect of the colon cancer tumor was recognized.

From the above, it was found that as in the case of the anti-PD-L1 antibody, by using curcumin in combination when an anti-PD-1 antibody is administered, a remarkable antiproliferative effect of the MC38 mouse colon cancer tumor is obtained by a synergistic effect of both.

(5) The influence on the proliferation of MC38 mouse colon cancer tumor due to the combined use of synthetic curcumin (5 mg/kg/mouse) and an anti-PD-1 antibody was examined.

As shown in FIG. 7, the size of the MC38 mouse colon cancer tumor showed a significantly smaller value in a case where a synthetic curcumin-HPMC complex (5 mg/kg/mouse) and an anti-PD-1 antibody were used in combination (Example 5) as compared with that in a case where the anti-PD-1 antibody was singly administered, and a remarkable antiproliferative effect of the colon cancer tumor was recognized.

From the above, it was found that even in a case where synthetic curcumin is used in combination when an anti-PD-1 antibody is administered, a remarkable antiproliferative effect of the MC38 mouse colon cancer tumor is obtained.

The invention claimed is:

1. A formulation, comprising:
Theracurmin®; and
at least one selected from the group consisting of an anti-PD-1 antibody, an anti-PD-L1 antibody, and an anti-PD-L2 antibody.

2. The formulation according to claim 1, wherein each of the anti-PD-1 antibody, the anti-PD-L1 antibody, and the anti-PD-L2 antibody is a humanized antibody.

3. The formulation according to claim 1, further comprising at least one selected from the group consisting of an immunostimulant and a cancer chemotherapeutic agent.

4. The formulation according to claim 1, comprising the anti-PD-1 antibody.

5. The formulation according to claim 1, comprising the anti-PD-L1 antibody.

6. The formulation according to claim 1, comprising the anti-PD-L2 antibody.

7. The formulation according to claim 1, further comprising a pharmaceutically acceptable carrier.

8. The formulation according to claim 1, further comprising at least one selected from the group consisting of an excipient, a binder, a disintegrant, a lubricant, a diluent, a stabilizer, a suspending agent, a pH adjuster, and an isotonizing agent.

* * * * *